United States Patent
Murad et al.

[19]

[11] Patent Number: 5,898,373
[45] Date of Patent: Apr. 27, 1999

[54] METHOD OF MONITORING A SITE FOR THE FUTURE PRESENCE OF TOXIC AGENTS

[76] Inventors: Edmond Murad, 20 Kenrick Ter., Newton, Mass. 02158; Charles P. Pike, 69 Locksley Rd., Lynnfield, Mass. 01940

[21] Appl. No.: 09/045,887

[22] Filed: Mar. 18, 1998

[51] Int. Cl.[6] .............................................. G08B 17/12
[52] U.S. Cl. ........................................................ 340/600
[58] Field of Search ............................. 340/600; 356/73, 356/301; 250/365, 361 C

[56] References Cited

U.S. PATENT DOCUMENTS

| | | | |
|---|---|---|---|
| 4,931,646 | 6/1990 | Koechner | 250/367 |
| 5,145,645 | 9/1992 | Zakin et al. | 422/98 |
| 5,168,265 | 12/1992 | Aslan | 340/600 |
| 5,257,085 | 10/1993 | Ulich et al. | 356/73 |
| 5,576,696 | 11/1996 | Adler | 340/600 |
| 5,600,307 | 2/1997 | Aslan | 340/600 |
| 5,691,700 | 11/1997 | Phelps et al. | 340/600 |

*Primary Examiner*—Jeffery A. Hofsass
*Assistant Examiner*—Toan N. Pham

[57] ABSTRACT

Sticky polymeric particles are planted upon a site to be remotely monitored over a substantial future time period for the presence of toxic target agents. An airborne vehicle positioned over the site directs a laser beam toward the site and if one or more toxic agents are present at the site, a return beam is produced having one or more known spectral signatures corresponding to the toxic target agents which are recognized by a photospectrometer in the airborne vehicle. Alternatively, a chemiluminescent reaction between the toxin and the particles can produce an alarm condition right at the monitored site.

20 Claims, 1 Drawing Sheet

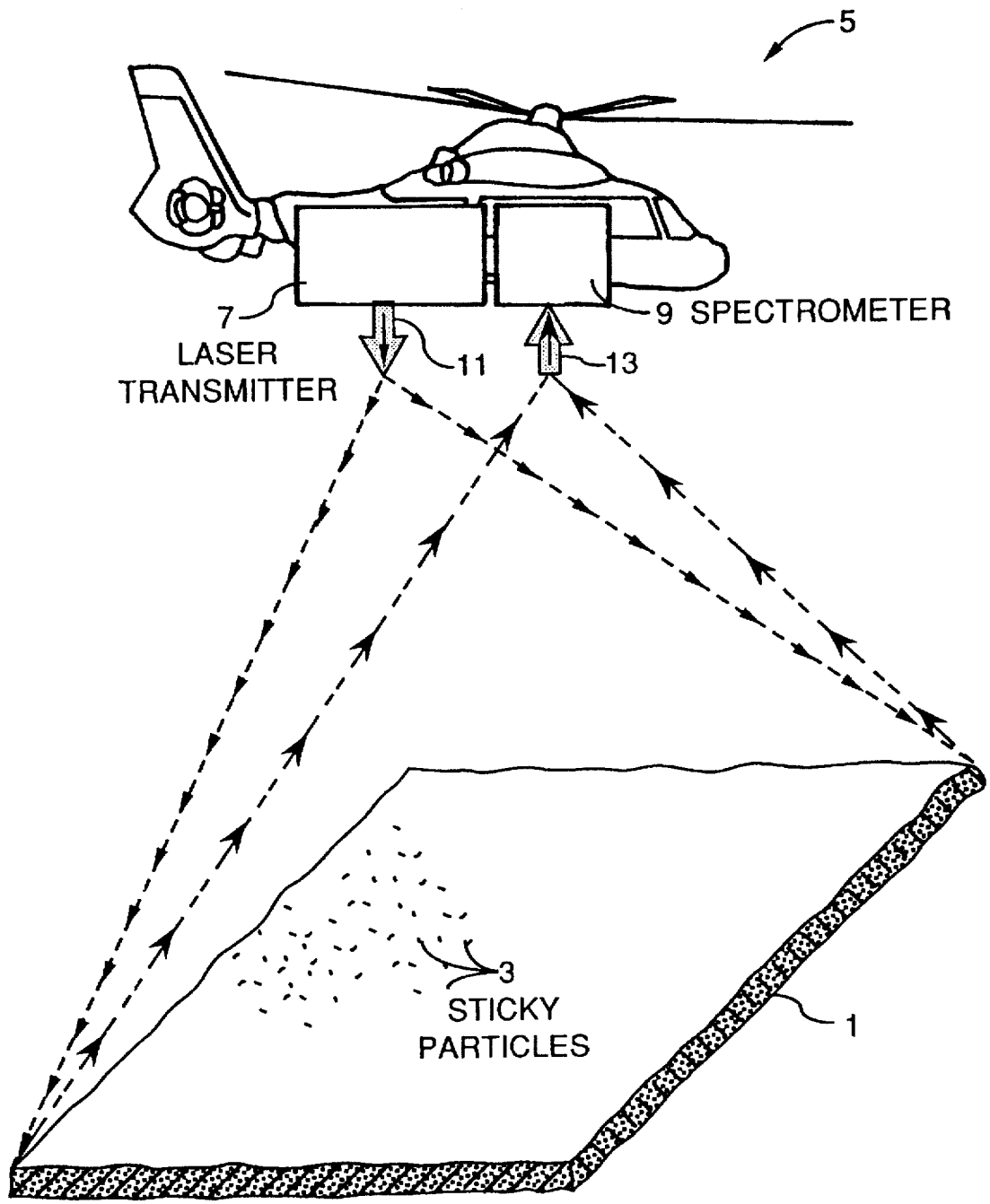

METHOD OF MONITORING A SITE FOR THE FUTURE PRESENCE OF TOXIC AGENTS

STATEMENT OF GOVERNMENT INTEREST

The invention herein may be made by or for the Government for governmental purposes without the payment of any royalty thereon.

BACKGROUND OF THE INVENTION

The present invention relates to the field of the detection of toxic materials in the environment.

The presence of environmental toxins such as chemical and biological agents can be a well known destructive threat to humans, animals and plant life in the environment. Rapid detection of such toxins is of the utmost importance in both the military and commercial sectors to maintain a healthy state of people and the environment. Threatening agents in a military, or even in a civilian environment, include nerve gas for example. In the civilian sector, terrorist attacks could result in the spreading of deadly poisons, and waste dumps could contain substances which should be further processed and disposed of to protect the environment. Such detection should often ideally be produced at a considerable distance from the site containing the toxic agent, such as from the air, where the close presence of the agent could be an immediate threat to the health of humans carrying out the detection process.

One suggested approach is to generate a moving gaseous body of particles suspended in a cloud like moving mass, which can be directed at a site suspected of containing target agents, such as one or more designated toxic materials. Such suspended particles could interact with the toxins to thereafter produce, upon illumination, a detectable effect such as fluorescence, phosphorescence or spectral absorption or reflectance of particular wavelengths of light. However, in certain situations, it is desirable to continuously monitor a particular known site for the presence of a toxin over a substantial period of time extending into the future, such as up to many weeks, so that the aforesaid cloud or moving body of detection agents would be dissipated, and thus no longer be continuously available to monitor the site. One such application could involve monitoring compliance with a disarmament agreement requiring removal of selected target agents from suspected sites within a political body.

SUMMARY OF A PREFERRED EMBODIMENT OF THE INVENTION

In order to meet the aforesaid desired objectives, sticky polymeric particles are scattered in the neighborhood of selected sites to be monitored over a future substantial time period, such as weeks or months, to detect particular target agents, including for example, classes of toxin such as chemical or biological weapons, agricultural pests or the like. The sticky polymeric dust particles, maintained in place due to their sticky property, react with these target agents, and the resulting changed electromagnetic signature of backscattered light is detected from the air using, for example, a manned aircraft, a low altitude unmanned airborne drone or satellite as a monitoring vehicle. A low power laser in the airborne vehicle illuminates the particles, and the changed electromagnetic signature is detected by a photospectrometer in the vehicle, to indicate the presence of the target agents in the monitored site. The result is remote, safe surveillance of areas to be monitored over a substantial future time period.

BRIEF DESCRIPTION OF THE DRAWING

Various features of the invention will become more apparent upon reading of the following description taken in conjunction with the sole FIGURE schematically illustrating one method of carrying out the invention.

DETAILED DESCRIPTION OF PREFERRED EMBODIMENTS OF THE INVENTION

For monitoring environmental conditions, lidar remote sensing systems have been developed, including differential absorption lidar systems designated DIAL. DIAL techniques employ slightly different wavelengths of laser generated light which are differentially absorbed and result in a back scattered return of light producing a particular known electromagnetic signature. Laser Focus World, April 1995, pages 87–94, describes such systems whereby satellite based remote sensing lasers illuminate target sites at earth's surface and the return electromagnetic signature is examined by spectroscopy within the satellite to determine the chemical composition of the target site under illumination. See also U.S. Pat. No. 5,257,085 and Laser Focus World, March 1994, pages 547–551, discussing wide area pollution monitoring employing fluorescence spectroscopy, and chemiluminescence.

High ultraviolet laser generated pulse energy has potential for the extremely important remote sensing of biological and chemical weapons, which could be present at a site under surveillance. An essential amino acid tryptophan is an important constituant of biological organisms, including biological weapons and agricultural pests. This substance has an absorption peak in the neighborhood of 280–290 nanometers which can produce a distinctive electromagnetic return signature, detectable by spectroscopy when the target site toxin is illuminated from a UV laser in a remote biological weapons detection system. See Laser Focus World, April 1994, pages 83–87. Similar returned electromagnetic signatures of back scattered light, known in the art, can be utilized in accordance with the present invention.

As indicated by the sole figure, the site to be placed under surveillance 1, contains the aforesaid sticky polymeric particles 3 which are dropped in a battlefield environment for example, or otherwise planted in an environment to be inspected in accordance with an arms control treaty. Micron sized polymer particles 3 are made of a material that will interact with one or more target toxins to result in a newly produced electromagnetic return signature upon being illuminated with excitation light 11 from laser transmitter 7 on board an aircraft performing the site monitoring mission. This return signature of the back scattered light 13 from particles 3 is detected by spectrometer 9 on board aircraft 5, and the target toxin, interacting with the sticky particles 3, is identified by the computer application of appropriate algorithms to the spectrometer readout spectrum representing the aforesaid electromagnetic signature of the back scattered light. The exact makeup of the sticky particles will relate to the nature of the anticipated target agent. If more than one target agent may be present, additional particle types having appropriate compositions will be planted in the area under surveillance.

Suitable polymers for reacting with highly toxic hydrazine vapor to produce recognizable back scattered return DIAL electromagnetic light signatures are disclosed in U.S. Pat. No. 5,145,645 entitled "Conductive Polymer Selective Species Sensor", incorporated by reference herein. It is also known in the art that tabun, sarin, soman and GF nerve agents can react with undoped one micron particles of conductive polymer poly (3,4 dimethylpyrrole) containing acetylcholinesterase. Other similar reactions which can be employed, are known in the art.

Methods of rendering the polymer particles 3 sticky will be readily apparent to workers skilled in the adhesive arts. The luminescent dust particles 3 can be incorporated into a liquid or aerosol spray adhesive, so that the dust particles can be dispersed at the same time as the spray. An appropriate adhesive is marketed under the trademark "Krylon". An alternative method of dispersal is to spread the polymer spray in the area first, and follow quickly with the luminescent dust, so that the dust adheres to the surface of the applied adhesive coating. In either case, the luminescent dust is the active agent that will detect the hazardous chemical or other particulate threat.

In accordance with a more passive method of practicing the invention, the dust will be doped with a chemical that reacts with the hazardous chemical in a chemiluminescent reaction, whereby light will be radiated upon exposure to the hazardous chemical. In situ surveillance detectors such as photometers, cameras, television monitors and the like will detect this chemiluminescent signal and will issue an alarm. In this case, the detectors need not be remotely located, in contrast with the air born equipment described in connection with the sole FIGURE.

Since other variations in the aforesaid method will become apparent to those skilled in the art, the scope of the invention is to be limited solely by the terms of the following claims and art recognized equivalents thereof. For example, it may be practicable to produce remotely detectable luminescence of the particles 3 without illuminating them with laser light or otherwise exciting them. The term "airborne vehicle" is intended to include satellites in space.

What is claimed is:

1. A method of signaling the presence of particular target agents in a surveillance area over a substantial time period up to several weeks or more, comprising the steps of:
   (a) positioning numerous solid particles, sticky enough to maintain said solid particles in place upon said surveillance area, and which can interact with said target agents to produce an electromagnetic signature indicative of the presence of said target agents; and
   (b) detecting said electromagnetic signature in order to indicate the presence of said target agents in the surveillance area.

2. The method of claim 1 wherein step (b) comprises detecting light produced by a chemiluminescent reaction between said solid particles and said target agents.

3. The method of claim 2 wherein step (b) is carried out at said surveillance area.

4. The method of claim 1 comprising illuminating said solid particles with laser light.

5. The method of claim 4 wherein said laser light is ultraviolet light.

6. The method of claim 1 wherein said electromagnetic signature is produced by radiating said particles with excitation radiation to produce responsive back scattered radiation, detected in accordance with step (b).

7. The method of claim 4 wherein said electromagnetic signature is produced by radiating said particles with excitation radiation to produce responsive back scattered radiation, detected in accordance with step (b).

8. The method of claim 5 wherein said electromagnetic signature is produced by radiating said particles with excitation radiation to produce responsive back scattered radiation, detected in accordance with step (b).

9. A method of signaling the presence of particular target agents in a predetermined surveillance area over a substantial time period up to several weeks or more, comprising the steps of:
   (a) positioning numerous solid particles within said surveillance area sticky enough to maintain said solid particles in place within said surveillance area, said particles being capable of interacting with said target agents to produce an electromagnetic signature indicative of the presence of said target agents;
   (b) illuminating said solid particles with excitation radiation for producing a back scattered return beam having a particular electromagnetic return signature if said target agent is present in said predetermined surveillance area; and
   (c) detecting said particular electromagnetic return signature in order to indicate the presence of said target agents in the surveillance area.

10. The method of claim 9 wherein step (b) is carried out by illuminating said particles with laser light.

11. The method of claim 10 wherein said laser light is ultraviolet light.

12. The method of claim 9 wherein steps (b) and (c) are performed in a remote airborne vehicle.

13. The method of claim 10 wherein steps (b) and (c) are performed in a remote airborne vehicle.

14. The method of claim 11 wherein steps (b) and (c) are performed in a remote airborne vehicle.

15. A method of signaling the presence of particular target agents in a predetermined surveillance area over a substantial time period up to several weeks or more, comprising the steps of:
   (a) positioning numerous micron-size solid particles within said surveillance area sticky enough to maintain said solid particles in place within said surveillance area, said particles being capable of being altered in the presence of said target agents to produce an electromagnetic signature indicative of the presence of said target agents;
   (b) illuminating said solid particles with excitation radiation for producing a back scattered return beam having a particular electromagnetic return signature in response to said particles being altered due to the target agent being present in said predetermined surveillance area; and
   (c) detecting said particular electromagnetic return signature in order to indicate the presence of said target agents in the surveillance area.

16. The method of claim 15 wherein step (b) is carried out by illuminating said particles with laser light.

17. The method of claim 16 wherein said laser light is ultraviolet light.

18. The method of claim 15 wherein steps (b) and (c) are performed in a remote airborne vehicle.

19. The method of claim 16 wherein steps (b) and (c) are performed in a remote airborne vehicle.

20. The method of claim 17 wherein steps (b) and (c) are performed in a remote airborne vehicle.

* * * * *